(12) United States Patent
Hu et al.

(10) Patent No.: US 11,260,011 B2
(45) Date of Patent: Mar. 1, 2022

(54) USE OF NEOHESPERIDIN

(71) Applicant: NATURAL MEDICINE INSTITUTE OF ZHEJIANG YANGSHENGTANG CO., LTD., Zhejiang (CN)

(72) Inventors: Liu Hu, Zhejiang (CN); Hongying Lan, Zhejiang (CN)

(73) Assignee: NATURAL MEDICINE INSTITUTE OF ZHEJIANG YANGSHENGTANG CO., LTD., Zhejiang (CN)

( * ) Notice: Subject to any disclaimer, the term of this patent is extended or adjusted under 35 U.S.C. 154(b) by 88 days.

(21) Appl. No.: 16/407,482

(22) Filed: May 9, 2019

(65) Prior Publication Data

US 2019/0274941 A1    Sep. 12, 2019

Related U.S. Application Data

(62) Division of application No. 14/359,971, filed as application No. PCT/CN2011/082950 on Nov. 25, 2011, now Pat. No. 10,335,356.

(51) Int. Cl.

| A61K 36/75 | (2006.01) |
| A61K 8/60 | (2006.01) |
| A61Q 19/00 | (2006.01) |
| A61K 31/7048 | (2006.01) |
| A61K 8/9789 | (2017.01) |

(52) U.S. Cl.
CPC ........... *A61K 8/602* (2013.01); *A61K 8/60* (2013.01); *A61K 31/7048* (2013.01); *A61K 36/75* (2013.01); *A61Q 19/00* (2013.01); *A61Q 19/005* (2013.01); *A61K 8/9789* (2017.08)

(58) Field of Classification Search
None
See application file for complete search history.

(56) References Cited

U.S. PATENT DOCUMENTS

| 6,221,357 B1 | 4/2001 | Bok et al. |
| 2008/0008673 A1 | 1/2008 | Willemin et al. |
| 2008/0311229 A1 | 12/2008 | Nam |
| 2010/0166851 A1 | 7/2010 | Dallas |
| 2013/0131160 A1 | 5/2013 | Hu |

FOREIGN PATENT DOCUMENTS

| CN | 1836665 A | 9/2006 |
| CN | 101797216 A | 8/2010 |
| CN | 102166181 A | 8/2011 |
| CN | 102258528 A | 11/2011 |
| FR | 2825627 A1 | 12/2002 |
| JP | 2001026542 A | 1/2001 |
| JP | 2004035440 A | 2/2004 |
| JP | 2005170804 A | 6/2005 |
| JP | 2007056035 A | * 3/2007 |
| JP | 2007056035 A | 3/2007 |
| KR | 101064570 B1 | 9/2011 |
| WO | 2006103939 A1 | 10/2006 |

OTHER PUBLICATIONS

Notification of Reasons for Refusal Korean Patent Application No. 10-2014-7015756 dated Jun. 28, 2017 with English translation.
Korean Office Action dated Nov. 29, 2016 for Application No. 10-2014-7015756.
Kiefer et al., "Citrus flavonoids with skin lightening effects—safety and efficacy studies", SOFW-Journal, 2010, vol. 136, pp. 46-54.
International Search Report for PCT/CN2011/082950 dated Oct. 6, 2015.
Yue, Xuezhuang, Effects of Hesperidin, Licorice and EGCG on Melanogenesis, Skin Microcirculation and Secretion of VEGF of Keratinocytes, China Doctor/Master Dissertation Full-text database (Doctor) Medical and health science and technology, No. 12, 2006, Nov. 16, 2006 (Nov. 16, 2006)-Dec. 15, 2006 (Dec. 15, 2006), p. E075-3.
Japanese Office Action dated Oct. 29, 2015 for Application No. 2014-542664.
Jayaprakasha et al. (2007) Bioorganic & Medicinal Chemistry 15: 4923-4932.
Nizamutdinova et al. (2008) International Immunopharmacology 8, 670-678.
Raskin et al. (2004) Current Pharmaceutical Design, 10, 3419-3429.
Revilla et al. (1998) J. Agric. Food Chem, 46, 4592-4597.

* cited by examiner

*Primary Examiner* — Russell G Fiebig
(74) *Attorney, Agent, or Firm* — Pillsbury Winthrop Shaw Pittman, LLP

(57) ABSTRACT

The present invention discloses a use of neohesperidin or a neohesperidin-containing plant extract in the manufacture of a product for improving and/or promoting skin microcirculation, or for eliminating and/or alleviating diseases or conditions associated with poor skin microcirculation. The present invention also discloses a composition comprising an effective amount of neohesperidin or a neohesperidin-containing plant extract, and to a method for improving and/or promoting skin microcirculation, or eliminating and/or alleviating diseases or conditions associated with poor skin microcirculation, by using neohesperidin. The skin microcirculation of the present invention is preferably eye skin microcirculation.

18 Claims, No Drawings

USE OF NEOHESPERIDIN

CROSS-REFERENCE TO RELATED APPLICATIONS

This application is a divisional of U.S. patent application Ser. No. 14/359,971, filed on Jul. 24, 2014, which is a National Stage of PCT/CN2011/082950, filed Nov. 25, 2011, each hereby expressly incorporated by reference in its entirety and each assigned to the assignee hereof.

TECHNICAL FIELD

The present invention relates to a novel use of neohesperidin, particularly, a novel use in cosmetics, more particularly, a use of neohesperidin as a chemical ingredient for improving skin microcirculation, in particular, a use in dispelling under-eye dark circle.

BACKGROUND ART

Eye skin in human bodies is different from skin of other parts in human bodies in structure. Firstly, the skin around eyes, which is above zygoma and in the flanks of nose bridge, is "transportation sites" of blood vessels and lymph. In this region, face venules converge, and blood vessels are fine and abundant. If eye skin microcirculation is deficient, it will lead to poor blood circulation or tissue edema resulting in blood stasis and hematoma, water hoarding. Meanwhile, skin around eyes is very thin, only 1/10 thickness of skin of other parts, and therefore the skin around eyes exhibits atropurpureus and forms under-eye dark circle easily after light reflection. Moreover, factors, such as fatigue, pressure, and sleep insufficiency, are important factors responsible for microcirculation dysfunction. As growing older, the thickness of skin decreases by about 6% per 10 years, and therefore under-eye dark circle is more obvious. Thus, no matter for a short or long term, women in different ages experienced to be perplexed or are perplexed all the time by under-eye dark circle, and need to be improved by improving microcirculation of skin around eyes.

It is reported in papers that many natural plants extracts can significantly improve skin microcirculation after administering them by routes, such as, orally and intravenously, wherein the natural plants extracts include, for example, extract of safflower, extract of *Salvia miltiorrhiza*, extract of ginkgo leaf, extract of *Ruscus aculeatus* L., extract of genista, extract of oranges and tangerines, extract of ginseng, and the like. Some papers also reported the effect of some monomeric ingredients extracted from said plant extracts, such as tanshinone, ginsenoside, β-aescin, ruscogenin, ginkgo flavone, and the like, on microcirculation after topical application of them to human skin. However, the results show that these chemical substances cannot significantly improve skin microcirculation after topical administration of them to skin surface.

Eye products for improving skin microcirculation (for example, improving eye skin microcirculation such as dispelling under-eye dark circle), as sold in market currently, emerge endlessly, most of which have some plant extracts added. However, on one hand, it is not clear which ingredient of the extracts or which class of ingredients of the extracts work, on the other hand, these products do not have a significant effect on dispelling under-eye dark circle. Most products for improving skin microcirculation (for example, for dispelling under-eye dark circle) did not bring about the effect as expected (such as the efficacy of dispelling under-eye dark circle) after being used by the consumers. Therefore, it is still a major research direction for the skilled in the art to look for chemical substances capable of improving skin microcirculation significantly after topical application, so as to develop products for improving skin microcirculation (for example, for improving eye skin microcirculation, such as, for dispelling under-eye dark circle), in particular, eye care products for dispelling under-eye dark circle.

Neohesperidin is a flavanone, derived from fruits of rutaceae plants of *Poncirus trifoliata*(L.)Raf., with a formula as follows:

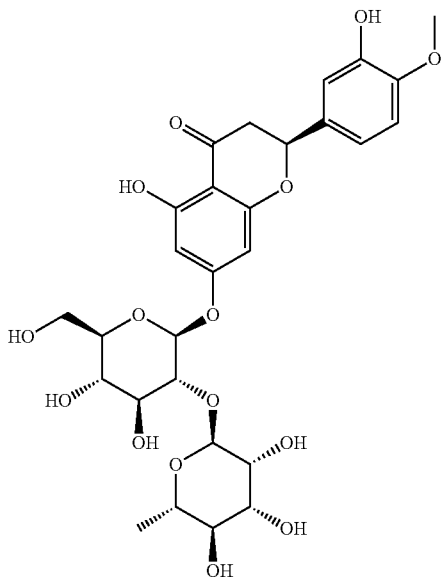 [SMILES: COc1ccc([C@@H]2CC(=O)c3c(O)cc(O[C@@H]4O[C@H](CO)[C@@H](O)[C@H](O)[C@H]4O[C@@H]4O[C@@H](C)[C@H](O)[C@@H](O)[C@H]4O)cc3O2)cc1O]

It has a molecular formula of $C_{28}H_{34}O_{15}$ and a molecular weight of 610.56, and mainly used in the preparation of novel type of sweeting agent of dihydrogenchalcone. It is reported in documents that neohesperidin is therapeutically effective on antianaphylaxis to some extent. However, it is not reported yet that neohesperidin is useful in improving skin microcirculation. Development of new products capable of improving skin microcirculation, particularly products capable of improving eye skin microcirculation, is still expected by a person skilled in the art.

CONTENTS OF THE INVENTION

The objective of the present invention is to provide a novel use of neohesperidin in improving skin microcirculation (for example, improving eye skin microcirculation such as dispelling under-eye dark circle). It is discovered in the present invention surprisingly that neohesperidin or a neohesperidin-containing plant extract effectively improves skin microcirculation, particularly eye skin microcirculation, more particularly effectively dispels under-eye dark circle. The present invention is accomplished on the basis of above discovery.

SUMMARY OF THE INVENTION

Thus, in a first aspect, the present invention provides a use of neohesperidin or a neohesperidin-containing plant extract in the manufacture of a product for improving and/or promoting skin microcirculation, or for eliminating and/or alleviating diseases or conditions associated with poor skin microcirculation, for example, in the manufacture of a product for improving and/or promoting skin microcirculation in a mammalian (particularly human), or for eliminating and/or alleviating diseases or conditions associated with poor skin microcirculation in a mammalian (particularly human).

The use according to the first aspect of the present invention, wherein the skin microcirculation is eye skin microcirculation.

The use according to the first aspect of the present invention, wherein the diseases or conditions associated with poor skin microcirculation are diseases or conditions associated with poor eye skin microcirculation.

The use according to the first aspect of the present invention, wherein the diseases or conditions associated with poor eye skin microcirculation are under-eye dark circles.

The use according to the first aspect of the present invention, wherein the neohesperidin-containing plant extract is an extract obtained by extracting from fruits of *Poncirus trifoliata*(L.)Raf.

The use according to the first aspect of the present invention, wherein the neohesperidin-containing plant extract is an extract obtained by extracting from fruits of *Poncirus trifoliata*(L.)Raf., and the extract comprises neohesperidin in an amount of not less than 50 wt % (weight %). In a preferred embodiment, the extract comprises neohesperidin in an amount of 60 wt % or more, 70 wt % or more, 80 wt % or more, 85 wt % or more, 90 wt % or more, or 95 wt % or more.

The use according to the first aspect of the present invention, wherein the product is a product for topical administration.

The use according to the first aspect of the present invention, wherein the product is a topical administration product for external skin use.

The use according to the first aspect of the present invention, wherein the product is a topical administration product for eye skin.

The use according to the first aspect of the present invention, wherein the product is a cosmetic.

The use according to the first aspect of the present invention, wherein the product is in a form of solution, emulsion, paste, cream, or gel.

The use according to the first aspect of the present invention, wherein the product comprises (1) neohesperidin or a neohesperidin-containing plant extract, and (2) a physiologically acceptable excipient.

The use according to the first aspect of the present invention, wherein the product comprises (1) neohesperidin or a neohesperidin-containing plant extract, and (2) a physiologically acceptable excipient; wherein the neohesperidin or the neohesperidin-containing plant extract accounts for 0.01 to 20 wt % of the total weight of the product, as calculated by weight of neohesperidin. In an embodiment, the neohesperidin or the neohesperidin-containing plant extract accounts for 0.01 to 15 wt %, 0.01 to 10 wt %, 0.05 to 15 wt %, 0.1 to 10 wt %, 0.2 to 10 wt %, or 0.2 to 5 wt % of the total weight of the product, as calculated by weight of neohesperidin.

In a second aspect, the present invention provides a composition, comprising (1) an effective amount of neohesperidin or a neohesperidin-containing plant extract, and optionally (2) a physiologically acceptable excipient.

The composition according to the second aspect of the present invention, comprises: (1) an effective amount of neohesperidin or a neohesperidin-containing plant extract, and optionally (2) a physiologically acceptable excipient; wherein the neohesperidin or the neohesperidin-containing plant extract accounts for 0.01 to 20 wt % of the total weight of the composition, as calculated by weight of neohesperidin. In an embodiment, the neohesperidin or the neohesperidin-containing plant extract accounts for 0.01 to 15 wt %, 0.01 to 10 wt %, 0.05 to 15 wt %, 0.1 to 10 wt %, 0.2 to 10 wt %, or 0.2 to 5 wt % of the total weight of the product, as calculated by weight of neohesperidin.

The composition according to the second aspect of the present invention, wherein the neohesperidin-containing plant extract is an extract obtained by extracting from fruits of *Poncirus trifoliata*(L.)Raf.

The composition according to the second aspect of the present invention, wherein the neohesperidin-containing plant extract is an extract obtained by extracting from fruits of *Poncirus trifoliata*(L.)Raf., and the extract comprises neohesperidin in an amount of not less than 50 wt %. In a preferred embodiment, the extract comprises neohesperidin in an amount of 60 wt % or more, 70 wt % or more, 80 wt % or more, 85 wt % or more, 90 wt % or more, or 95 wt % or more.

The composition according to the second aspect of the present invention, is a product improving and/or promoting skin microcirculation, or for eliminating and/or alleviating diseases or conditions associated with poor skin microcirculation. In one embodiment, the skin microcirculation is eye skin microcirculation. In one embodiment, the diseases or conditions associated with poor skin microcirculation are diseases or conditions associated with poor eye skin microcirculation. In one embodiment, the diseases or conditions associated with poor eye skin microcirculation are under-eye dark circles.

The composition according to the second aspect of the present invention, is a product for topical administration.

The composition according to the second aspect of the present invention, is a topical administration product for external dermatological use.

The composition according to the second aspect of the present invention, is a topical administration product for eye skin.

The composition according to the second aspect of the present invention, is a cosmetic.

The composition according to the second aspect of the present invention, is in a form of solution, emulsion, paste, cream, or gel.

In a third aspect, the present invention provides a method for improving and/or promoting skin microcirculation, or for eliminating and/or alleviating diseases or conditions associated with poor skin microcirculation in a subject in need thereof, comprising administering an effective amount of neohesperidin or a neohesperidin-containing plant extract to the subject.

The method according to the third aspect of the present invention, wherein the skin microcirculation is eye skin microcirculation.

The method according to the third aspect of the present invention, wherein the diseases or conditions associated with poor skin microcirculation are diseases or conditions associated with poor eye skin microcirculation.

The method according to the third aspect of the present invention, wherein the diseases or conditions associated with poor eye skin microcirculation is under-eye dark circle.

The method according to the third aspect of the present invention, wherein the neohesperidin-containing plant extract is an extract obtained by extracting from fruits of *Poncirus trifoliata*(L.)Raf.

The method according to the third aspect of the present invention, wherein the neohesperidin-containing plant extract is an extract obtained by extracting from fruits of *Poncirus trifoliata*(L.)Raf., and the extract comprises neohesperidin in an amount of not less than 50 wt %. In a preferred embodiment, the extract comprises neohesperidin in an amount of 60 wt % or more, 70 wt % or more, 80 wt % or more, 85 wt % or more, 90 wt % or more, or 95 wt % or more.

The method according to the third aspect of the present invention, wherein the effective amount of neohesperidin or a neohesperidin-containing plant extract is administered in a form of a topical administration product.

The method according to the third aspect of the present invention, wherein the effective amount of neohesperidin or a neohesperidin-containing plant extract is administered in a form of a topical administration product for external dermatological use.

The method according to the third aspect of the present invention, wherein the effective amount of neohesperidin or a neohesperidin-containing plant extract is administered in a form of a topical administration product for eye skin.

The method according to the third aspect of the present invention, wherein the effective amount of neohesperidin or a neohesperidin-containing plant extract is administered in a form of cosmetic.

The method according to the third aspect of the present invention, wherein the effective amount of neohesperidin or a neohesperidin-containing plant extract is administered in a form of solution, emulsion, paste, cream, or gel.

The features of any aspect of the present invention or of any embodiment of the aspect are also applicable to any other embodiment of the aspect or to any other aspect or any embodiment of the another aspect.

DETAILED DESCRIPTION OF THE INVENTION

The aspects and characteristics of the present invention are further described as follows.

All the documents cited in the present invention are incorporated herein by reference in its entirety, and if the meanings expressed in the documents are different from those in the present invention, the expressions in the present invention will control. In addition, the terms and phases used in the present invention have the general meanings recognized by a person skilled in the art. Even so, the present invention still tries to expound and explain the terms and phases as detailed as possible. If the terms and phases mentioned herein are not consistent with the well-known meanings, the meanings expressed in the present invention will control.

As described herein, the term "skin microcirculation" refers to microvascular net under dermal layer of skin, which is a terminal part of circulation, belongs to blood capillary, is a connection point between artery and vein, and is a place where material interchange of blood and tissue cells is carrier out. Skin microcirculation is a complex dynamic system, which has an important effect on skin color, temperature adjustment, skin metabolism and transdermal transport, and therefore directly affects the health of skin.

As described herein, the term "diseases or conditions associated with poor skin microcirculation" refers to pathogenic or nonpathogenic physical status or abnormal condition resulted from poor topical skin microcirculation or topical skin microcirculation disorder, such as, dermatitis, pigmentation, skin aging, pale skin, bloodshot on face, topical skin stasis and hematoma, topical water hoarding, and under-eye dark circle.

As described herein, the term "improving", "promoting", "eliminating", and "alleviating", for example, in the expressions "improving and/or promoting skin microcirculation" and "for eliminating and/or alleviating diseases or conditions associated with poor skin microcirculation" as described herein, refers to the generation of a beneficent effect on pathogenic or nonpathogenic physical status or abnormal condition resulted from poor topical skin microcirculation or topical skin microcirculation disorder, for example, improvement of topical skin microcirculation, promotion of topical skin microcirculation, elimination of pathogenic or nonpathogenic physical status or abnormal condition resulted from poor topical skin microcirculation or topical skin microcirculation disorder, and alleviation of pathogenic or nonpathogenic physical status or abnormal condition resulted from poor topical skin microcirculation or topical skin microcirculation disorder, for example, improvement of bloodshot eyes, elimination of pigmentation, eliminating hydroncus, alleviation of stasis and hematoma, elimination of under-eye dark circle, and the like.

As described herein, the term "physiologically acceptable" means that substances are physiologically compatible, particularly, may be used in a product for external dermatological use when contacting skin, for example, without bringing about side effects such as irritability to skin. Particularly, for example, diluents, surfactants, thickeners, emollients, etc. may be used in cosmetics.

As described herein, the term "an effective amount" refers to an dose that can accomplish the treatment, prevention, reduction and/or alleviation of the diseases or conditions of the present invention in a subject.

As described herein, the term "composition" also refers to "cosmetic", "cosmetic composition", "pharmaceutical composition", all of which may be used in individuals for the treatment, prevention, reduction and/or alleviation of the diseases, conditions, or physical status of the present invention.

As described herein, the term "individual" may further refer to "subject", "patient" or other animal which are administered with the composition of the present invention to improve and/or promote the skin microcirculation appeared in them or to eliminate and/or alleviate diseases or conditions associated with poor skin microcirculation appeared in them, particularly, mammal, such as human, dog, monkey, bovine, horse, etc., in particular, human.

As described herein, the term "eye skin microcirculation" refers to microcirculation of skin around eyes.

According to the present invention, the neohesperidin may be extracted from fruits of plants of Rutaceae or from aerial part of *Galium mollugo* linn. or may be synthesized by chemical methods known in the art or be obtained by biotransformation. The neohesperidin may be a pure compound, or an extract containing neohesperidin in an amount of not less than 50% (w/w). In the present invention, as calculated by the weight of pure compound of neohesperidin, the neohesperidin is present in a concentration of 0.01%-20% (w/w), preferably 0.05%-15% (w/w), most preferably 0.1%-10% (w/w) in the composition of the present invention.

The present invention also comprises a cosmetic skin care composition comprising neohesperidin.

The present invention relates to a cosmetic skin care composition comprising (1) neohesperidin present in an amount of 0.1%-10% by weight; and (2) cosmetically acceptable vehicles.

The neohesperidin used in the composition of the present invention is to achieve the effect of dispelling under-eye dark circle.

The composition and method of the present invention further comprises cosmetically acceptable vehicles as the diluents, dispersants or carriers of active ingredient in the composition, to promote the distribution of the composition when applying the composition to skin.

Vehicles other than water comprise liquid or solid emollients, surfactants, solvents, and thickeners.

Active ingredients of various types may be present in the cosmetic composition of the present invention. Active substances are defined as substances different from emollients and ingredients merely improving physical properties of the composition.

In one embodiment, the present invention provides a composition has the following formulation.

| Ingredients | weight/weight |
| --- | --- |
| Methyl glucose sesqui-stearate | 0.5-5 wt % |
| dimethyl siloxane | 0.5-5 wt % |
| cetanol/octadecanol | 1-5 wt % |
| Dicapryl carbonate | 2-8 wt % |
| propyl heptyl octanoate | 1-5 wt % |
| lecithin | 1-5 wt % |
| Xanthan Gum | 0.1-2 wt % |
| 1,3-butanediol | 1-10 wt % |
| EDTA-2Na | 0.1-2 wt % |
| glycerin | 1-5 wt % |
| triethanolamine | 1-5 wt % |
| Lactic acid | an appropriate amount to adjust pH to a value from 4.0 to 6.0 |
| preservative | an appropriate amount |
| neohesperidin or a neohesperidin-containing extract | 0.01-20 wt %, 0.01-15 wt %, 0.01-10 wt %, 0.05-15 wt %, 0.1-10 wt %, 0.2-10 wt %, or 0.2-5 wt %, as calculated by weight of neohesperidin |
| water | added to 100% |

In accordance with the present invention, under-eye dark circle may be reduced or eliminated by topical application of neohesperidin.

The present invention relates to a novel use of neohesperidin in cosmetics, particularly a novel use of neohesperidin as a chemical ingredient for improving skin microcirculation in dispelling under-eye dark circle. Preferably, in the use, the neohesperidin is present in amount of 0.01%-10% by weight of the composition.

For better utilization of neohesperidin, the present invention studies the effect of topical administration of neohesperidin to skin surface on promoting microcirculation. The results show that after topical application of neohesperidin, skin microcirculation is significantly improved. The applicant applied neohesperidin to eye care products and found that it could significantly dispel under-eye dark circle.

SPECIFIC MODES FOR CARRYING OUT THE INVENTION

The present invention is further described by the following examples. However, the scope of the present invention is not limited to the following examples. The skilled in the art could understand that any change and modification may be made to the present invention without departing from the spirit and scope of the present invention.

The present invention generally and/or specifically describes the materials and experimental methods used in the present invention. Although many materials and operation methods used for achieving the purpose of the present invention are well known in the art, the present invention still describe them as detailed as possible. In the context of the present invention, unless indicated otherwise, % represent wt %, i.e. percentage by weight.

Example 1: Observing the Effect of Topical Application of Neohesperidin on Skin Microcirculation by Laser Doppler The experimental method for promoting microcirculation: Male *Oryctolagus cuniculus* weighted 3.0-3.5 kg were used. After shaving the hair on the back of the *Oryctolagus cuniculus*, 10 points for testing blood flow were marked with a marker pen on the hairless skin of the rabbit, i.e. 5 points for each of the right side and the left side, and aorta was avoided when drawing the points. Before smearing the sample, the basic values of blood flow at the 10 points of rabbits of each experimental group were determined by Laser Doppler Flowmetery. The rabbits of each group had blank solution smeared on the left back and had a neohesperidin-containing solution smeared on the right back(for three groups of animals, the concentration of the solutions were 0.5% (w/v), 1% (w/v) and 2% (w/v), respectively, 0.1 ml for each animal), three rabbits were used in parallel for each concentration. 2% (w/v) solution was orally administrated by a similar method in a volume 100 times compared to the volume used in the group wherein the 2% (w/v) solution was administered by smearing. After administration, the blood flow value was determined every hour at the same point by Laser Doppler Flowmetery for 24 h, and the variation index of blood flow was calculated to evaluate the effect of neohesperidin on the back blood of rabbits, wherein a higher variation index of blood flow indicated a better effect of promoting microcirculation. The experimental results were statistically analyzed by SPSS11.5 software, and t-test was applied to the measured data to evaluate the experimental results. When $P<0.1$, the data may be regarded as statistically significant. In the results of Table 1, all the time points with $P<0.1$ in the 24-h test were listed.

TABLE 1

The effect of neohesperidin at different concentrations on promoting skin microcirculation in domestic rabbits

| Neohesperidin concentration | Working time point | P value as compared to the blank side |
| --- | --- | --- |
| 0.5%, smearing | 6 h | p < 0.05 |
| 1%, smearing | 2 h | p < 0.05 |
|  | 3 h | p < 0.05 |
| 2%, smearing | 5 h | p < 0.05 |
|  | 2 h | p < 0.01 |
|  | 4 h | p < 0.05 |
|  | 5 h | p < 0.05 |
|  | 6 h | p < 0.05 |
| 2%, orally | — | — |

Note:
"—" represents the time point at which P < 0.1 did not appear during the 24 h test when 2% solution was administered orally.

The experimental results showed that after smearing the backs of rabbits with samples comprising different concentrations of neohesperidin, blood flow in skin microvessels was significantly enhanced in rabbits, as compared to the blank side.

Example 2: The Effect of Neohesperidin on Dispelling Under-Eye Dark Circle

Method: 8-week comparison experiments of two formulations at two sides of eyes were used in the study.

In the study, 50 volunteers with medium and severe under-eye dark circle were recruited in the study, to allow the effective number of each paired comparison group to be 15. The subjects were randomly assigned and the compositions were used in the left/right side equivalently, wherein one side of the eyes was smeared with the composition comprising neohesperidin, and the other side of the eyes was smeared with the composition comprising no neohesperidin, for 8 weeks. Efficacy evaluation was made as to the effect of dispelling under-eye dark circle at Week 0 (before treatment), 2, 4, 6 and 8.

Efficacy evaluation method: A photo of eyes of the subject taken at Day 0 of the experiment was used as the baseline data, and photos were taken at Week 2, 4, 6 and 8 of the experiment. Lab system of photoshop software was used to calculate and analyze the colority, wherein L represented the white degree of eye skin, a higher L value indicated a whiter skin. After comparison with the baseline data, SPSS statistic data was used to evaluate the efficacy of the products. When $P<0.1$, the data may be regarded as statistically significant.

The basic formulations in Table 2 and the compositions in Table 3 were used in the subjects for test.

TABLE 2

Basic formulations

| Ingredients | weight/weight |
|---|---|
| Methyl glucose sesqui-stearate | 1.2% |
| dimethyl siloxane | 1.0% |
| cetanol/octadecanol | 3% |
| Dicapryl carbonate | 4% |
| propyl heptyl octanoate | 2% |
| lecithin | 2.5% |
| Xanthan Gum | 0.3% |
| 1,3-butanediol | 4% |
| EDTA-2Na | 0.2% |
| glycerin | 2.0% |
| triethanolamine | 2% |
| Lactic acid | an appropriate amount to adjust pH to a value from 4.0 to 6.0 |
| preservative | an appropriate amount |
| water | added to 100% |

TABLE 3

Composition

| Composition | Ingredients |
|---|---|
| 1 | basic formulation |
| 2 | basic formulation + 0.5% neohesperidin |
| 3 | basic formulation + 2.0% neohesperidin |
| 4 | basic formulation + 10.0% neohesperidin extract (comprising 50% neohesperidin) |

The following paired comparisons were carried out:

Paired comparison 1: Composition 1 (basic formulation) vs Composition 2(basic formulation+0.5% neohesperidin);

Paired comparison 2: Composition 1 (basic formulation) vs Composition 3(basic formulation+2% neohesperidin);

Paired comparison 3: Composition 1 (basic formulation) vs Composition 4(basic formulation+10% neohesperidin extract).

The results were listed in Tables 4A to 4C:

TABLE 4A

The average improvement of under-eye dark circle by Paired comparison 1

| Week | basic formulation # | basic formulation + 0.5% neohesperidin |
|---|---|---|
| 0 | 0 | 0 |
| 2 | 0.8% | 0.8% |
| 4 | 1.0% | 1.2% |
| 6 | 1.5% | 2.2%** |
| 8 | 1.2% | 2.2%** |

**basic formulation + 0.5% neohesperidin provided a significantly greater improvement than basic formulation after using it for 6 weeks ($P < 0.05$).
basic formulation without active ingredient also generated a change, the accuracy of the experiments would be enhanced by deduction of the change. The factors responsible for the change generated by basic formulation might include, but be not limited to, non-objective factors such as the stimulating effect of the basic formulation itself, stimulation by heat and cold, emotion, and luminance of the photographic environment. These factors might be responsible for a change in L value, thereby reducing the objectivity of the experimental results. Thus, experimental conditions should be stringently controlled during the experiment. In the experimental method, self-control was set in the right and left eyes so as to eliminate or balance the effect of unrelated variants during the experiment to the maximum extent. Therefore, the difference between the experimental group and the control group might be regarded as the effect resulted from the experimental variants. For example, in the Example, the experimental results showed that the L value, on the side where basic formulation was smeared, increased to different extents at different times in the test, indicating that non-objective factors had a certain effect on the L value under the experimental conditions. However, the L value, on the side where neohesperidin was smeared, increased to a larger extent and was significant as compared to the former, indicating that the significance was resulted from neohesperidin.

TABLE 4B

The average improvement of under-eye dark circle by Paired comparison 2

| Week | basic formulation | basic formulation + 2% neohesperidin |
|---|---|---|
| 0 | 0 | 0 |
| 2 | 1.2% | 1.5% |
| 4 | 1.0% | 2.3%** |
| 6 | 1.5% | 2.5%** |
| 8 | 1.5% | 2.9%** |

**basic formulation + 2% neohesperidin provided a significantly greater improvement than basic formulation after using it for 4 weeks ($P < 0.05$).

TABLE 4C

The average improvement of under-eye dark circle by Paired comparison 3

| Week | basic formulation | basic formulation + 10% neohesperidin extract |
|---|---|---|
| 0 | 0 | 0 |
| 2 | 1.5% | 2.5%** |
| 4 | 1.8% | 3.0%** |
| 6 | 2.0% | 3.2%** |
| 8 | 1.2% | 3.8%** |

**basic formulation + 10% neohesperidin extract provided a significantly greater improvement than basic formulation after using it for 2 weeks ($P < 0.05$).

Said paired comparison results showed that the composition comprising neohesperidin significantly improved under-eye dark circle as compared with the composition comprising no neohesperidin. The Examples indicated that neohesperidin was useful for improving skin microcirculation, particularly eye skin microcirculation, in particular, was useful as cosmetic skin care product for dispelling under-eye dark circle.

The above-mentioned examples illustrate the composition for topical application according to the present invention, which may be processed by conventional means. They are suitable for cosmetic skin care use. In particular, the compositions are suitable for dispelling under-eye dark circle to improve appearance and feeling of eye skin.

What is claimed is:

1. A composition for improving and/or promoting skin microcirculation, or eliminating and/or alleviating diseases or conditions associated with poor skin microcirculation, comprising an effective amount of neohesperidin or a neohesperidin-containing plant extract, and a physiologically acceptable excipient;
the neohesperidin-containing plant extract being an extract obtained by extracting from fruits of *Poncirus trifoliata*(L)Raf, the extract comprising neohesperidin in an amount of not less than 50 wt %,
the composition comprising neohesperidin or a neohesperidin-containing plant extract in an amount of from 0.1-10 wt % of the total weight of the composition, as calculated by weight of neohesperidin, and physiologically acceptable excipients selected from the group consisting of:

| Ingredients | weight/weight |
| --- | --- |
| Methyl glucose sesqui-stearate | 1.2% |
| dimethyl siloxane | 1.0% |
| cetanol/octadecanol | 3% |
| Dicapryl carbonate | 4% |
| propyl heptyl octanoate | 2% |
| lecithin | 2.5% |
| Xanthan Gum | 0.3% |
| 1,3-butanediol | 4% |
| EDTA-2Na | 0.2% |
| glycerin | 2.0% |
| triethanolamine | 2% |
| Lactic acid | an appropriate amount to adjust pH to a value from 4.0 to 6.0 |
| preservative | an appropriate amount |
| water | added to 100% | wherein the composition improves and/or promotes skin microcirculation, or eliminates and/or alleviates diseases or conditions associated with poor skin microcirculation,
wherein the composition comprises neohesperidin or a neohesperidin-containing plant extract in a form and amount selected from the group consisting of: 0.5% neohesperidin; 2.0% neohesperidin; and 10% neohesperidin extract comprising 50% neohesperidin, and
wherein the composition comprises at least methyl glucose sesqui-stearate and propyl heptyl octanoate as excipients.

2. The composition of claim 1, which is a product for topical administration.

3. A method for improving and/or promoting skin microcirculation, or for eliminating and/or alleviating diseases or conditions associated with poor skin microcirculation comprising administering to a subject in need thereof the composition of claim 1.

4. The method of claim 3, wherein the skin microcirculation is eye skin microcirculation.

5. The method of claim 3, wherein the diseases or conditions associated with poor skin microcirculation are diseases or conditions associated with poor eye skin microcirculation.

6. The method of claim 3, wherein the diseases or conditions associated with poor eye skin microcirculation are under-eye dark circles.

7. The method of claim 3, wherein the neohesperidin-containing plant extract is an extract obtained by extracting from fruits of *Poncirus trifoliata*(L)Raf.

8. The method of claim 3, wherein the product is a product for topical administration.

9. The method of claim 3, wherein the product comprises neohesperidin or a neohesperidin-containing plant extract, and a physiologically acceptable excipient.

10. A composition for improving and/or promoting skin microcirculation, or eliminating and/or alleviating diseases or conditions associated with poor skin microcirculation, comprising an effective amount of neohesperidin or a neohesperidin-containing plant extract, and a physiologically acceptable excipient;
the neohesperidin-containing plant extract being an extract obtained by extracting from fruits of *Poncirus trifoliata*(L)Raf, the extract comprising neohesperidin in an amount of not less than 50 wt %,
the composition comprising neohesperidin or a neohesperidin-containing plant extract in an amount of from 0.1-10 wt % of the total weight of the composition, as calculated by weight of neohesperidin, and physiologically acceptable excipients consisting of:

| Ingredients | weight/weight |
| --- | --- |
| Methyl glucose sesqui-stearate | 0.5-5 wt % |
| dimethyl siloxane | 0.5-5 wt % |
| cetanol/octadecanol | 1-5 wt % |
| Dicapryl carbonate | 2-8 wt % |
| propyl heptyl octanoate | 1-5 wt % |
| lecithin | 1-5 wt % |
| Xanthan Gum | 0.1-2 wt % |
| 1,3-butanediol | 1-10 wt % |
| EDTA-2Na | 0.1-2 wt % |
| glycerin | 1-5 wt % |
| triethanolamine | 1-5 wt % |
| Lactic acid | an appropriate amount to adjust pH to a value from 4.0 to 6.0 |
| preservative | an appropriate amount |
| water | added to 100% | wherein the composition improves and/or promotes skin microcirculation, or eliminates and/or alleviates diseases or conditions associated with poor skin microcirculation,
wherein the composition comprises neohesperidin or a neohesperidin-containing plant extract in a form and amount selected from the group consisting of: 0.5% neohesperidin; 2.0% neohesperidin; and 10% neohesperidin extract comprising 50% neohesperidin.

11. The composition of claim 10, which is a product for topical administration.

12. A method for improving and/or promoting skin microcirculation, or for eliminating and/or alleviating diseases or conditions associated with poor skin microcirculation comprising administering to a subject in need thereof the composition of claim 10.

13. The method of claim 12, wherein the skin microcirculation is eye skin microcirculation.

14. The method of claim 12, wherein the diseases or conditions associated with poor skin microcirculation are diseases or conditions associated with poor eye skin microcirculation.

15. The method of claim 12, wherein the diseases or conditions associated with poor eye skin microcirculation are under-eye dark circles.

16. The method of claim 12, wherein the neohesperidin-containing plant extract is an extract obtained by extracting from fruits of *Poncirus trifoliata*(L.)Raf.

17. The method of claim 12, wherein the product is a product for topical administration.

18. The method of claim 12, wherein the product comprises neohesperidin or a neohesperidin-containing plant extract, and a physiologically acceptable excipient.

* * * * *